United States Patent [19]

Boesenberg et al.

[11] 4,370,489
[45] Jan. 25, 1983

[54] HERBICIDAL COMPOUNDS

[75] Inventors: Heinz Boesenberg, Langenhain; Gerhard Hörlein, Frankfurt am Main; Helmut Köcher, Hofheim; Peter Langelüddeke, Diedenbergen, all of Fed. Rep. of Germany

[73] Assignee: Hoechst Aktiengesellschaft, Frankfurt am Main, Fed. Rep. of Germany

[21] Appl. No.: 759,490

[22] Filed: Jan. 14, 1977

[30] Foreign Application Priority Data

Jan. 16, 1976 [DE] Fed. Rep. of Germany ....... 2601548

[51] Int. Cl.$^3$ ............................................. C07C 69/76
[52] U.S. Cl. ..................................... 560/62; 562/471; 260/501.1; 260/501.15; 260/501.16; 71/108; 71/116
[58] Field of Search .......... 260/413 C, 544 R, 501.15, 260/501.1, 501.16; 560/62; 562/471; 71/108, 116

[56] References Cited

U.S. PATENT DOCUMENTS 3,954,442  5/1976  Becker et al. ................. 260/473 G Primary Examiner—Paul J. Killos
Attorney, Agent, or Firm—Curtis, Morris & Safford

[57] ABSTRACT

Compounds of the formula

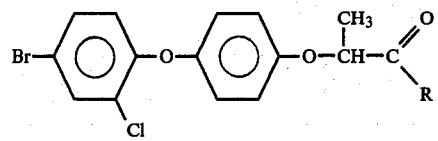

in which R represents hydroxyl, $(C_1-C_{10})$alkoxy, $(C_1-C_6)$alkylthio, $(C_2-C_4)$alkenyloxy, cyclohexyloxy, cyclopentyloxy, phenoxy or phenylthio both optionally substituted once or twice with halogen, benzyloxy, benzylthio or -O-cat in which "cat" stands for the cation of an inorganic or organic base, have a very good effect on wild oat, barnyard grass, bristle grass and ryegrass in a much lower concentration than known analogous compounds.

14 Claims, No Drawings

HERBICIDAL COMPOUNDS

The present invention relates to herbicidal compounds.

It is known from U.S. Pat. No. 3,954,442 that phenoxyphenoxy-alkane-carboxylic acids and the derivatives thereof exhibit a good selective herbicidal effect against weed grasses. In particular, compound A of the formula

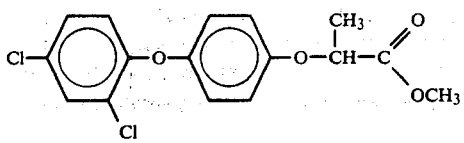

(methyl-2-[4-(2',4'-dichlorophenoxy)-phenoxy]-propionate), can be successfully used to combat wild oat, barnyard grass, bristle grass or ryegrass.

It has now been found that 2-[4-(2'-chloro-4'-bromophenoxy)-phenoxy]-propionic acid and the derivatives thereof (generically claimed but not specifically described in the above specification) have an even better herbicidal effect than the aforesaid compound against a number of weed grasses and a higher margin of safety.

The present invention therefore provides compounds of the formula I

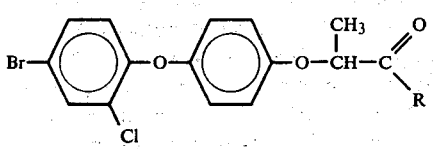

in which

R represents hydroxyl, $(C_1-C_{10})$alkoxy, $(C_1-C_6)$alkylthio, $(C_2-C_4)$alkenyloxy, cyclohexyloxy, cyclopentyloxy, phenoxy or phenylthio both optionally substituted once or twice with halogen, benzyloxy, benzylthio, or O-cat, in which cat stands for the cation of an inorganic or organic base.

Preferred compounds of formula I are esters with low molecular weight aliphatic alcohols $(R=(C_1-C_6)$alkoxy) and salts of the free acid (R=O-cat). Suitable cations are those of inorganic bases such as $Na^+$, $K^+$, $\frac{1}{2}Ca^{++}$, $NH_4^+$, or of organic bases such as $H_3N^+-CH_2-CH_2-OH$, $H_3N^+-CH_3$, $H_3N^+-C_2H_5$, $H_2N^+(CH_3)_2$, $H_2N^+(CH_3)C_4H_9(n)$, $HN^+(CH_2CH_2OH)_3$, $HN^+(C_2H_5)_3$, or the pyridinium cation.

The esters are obtained e.g. by reacting 4-(2'-chloro-4'-bromo)-phenoxyphenol with an α-halopropionic acid ester in the presence of an acid binding agent such as sodium or potassium carbonate or triethyl amine. In a modification of that process the phenoxyphenol is first reacted with a base to form the corresponding phenolate which in turn is reacted with the α-halopropionic acid ester. Both reactions are carried out in inert organic solvents such as acetone, chloroform, benzene, toluene and the like at elevated temperatures between room temperature and the boiling points of the solvents. The reaction is exemplified in the following diagram:

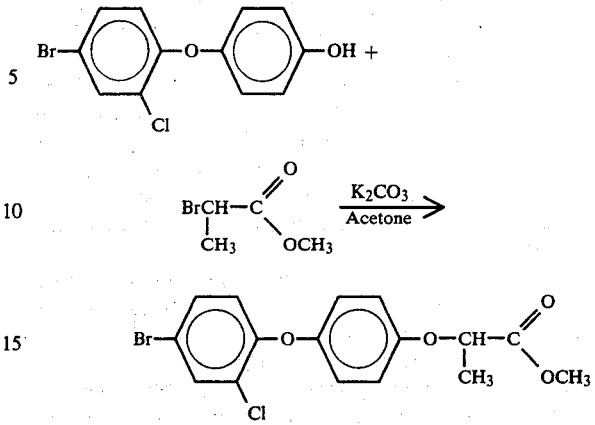

The esters thus obtained can then be saponified in a known manner to form the free acids which in turn can be transformed into other esters via the acid halides which are obtained by reacting the acids with halogenating agents such as $PCl_5$, $POCl_5$ or $SOCl_2$ and then reacted with corresponding alcohols or mercaptans in the presence of an acid binding agent as described above. The free acids can be converted into their salts by means of suitable inorganic or organic bases. All these reactions are generally known in the art and can be performed by any normally skilled person; they are moreover described in the Examples.

The starting material, i.e. 4-(2'-chloro-4'-bromo)-phenoxy phenol can be obtained e.g. by brominating o-chlorophenol at the 4-position; the 2-Cl-4-Br-phenol thus obtained is then reacted with p-nitrochlorobenzene to form 4-(2'-Cl-4'-Br-phenoxy)-nitrobenzene. This is then transformed into the desired 4-(2'-Cl-4'-Br-phenoxy)-phenol by successive reduction, diazotization and hydrolysis.

The present invention also provides herbicidal compositions containing one or several carried substances and as active ingredient a compound of the formula I. The compositions are effective in pre-emergence as well as post-emergence application against weed grasses, i.e. plants that belong to the botanic family of gramineae. Dicotyledonous crop plants, for example leguminosae (beans, peas), cotton, sugar beet, vegetables and many other are not damaged. It is remarkable that some gramineous crop plants such as barley and wheat are also left unharmed.

In particular, the compounds of the invention are effective against various types of wild oat (*Avena fatua, Avena ludoviciana*), annual blackgrass (*Alopecurus myosuroides*), bristle grasses (*Setaria faberii, Setaria lutescens, Setaria viridis*), barnyard grass (*Echinochloa crus-galli*), large crabgrass (*Digitaria sanguinalis*), ryegrass (*Lolium multiflorum*) and the like. The applied concentrations may vary within wide limits, for example of from 0.1 to 10 kg/hectare and preferably from 0.1 to 2.5 kg/hectare of active ingredient.

The compounds can be used in the form of wettable powders, emulsifiable concentrates, sprayable solutions, dusts, or granules, in admixture with the usual formulation auxiliaries.

Wettable powders are preparations that can be uniformly dispersed in water and contain, besides the active ingredient, a diluent or an inert substance, a wetting agent, for example polyoxethylated alkylphenols, or polyoxethylated oleyl- or stearyl-amines, and dispersing agents, for example the sodium salt of lignin-sulfonic acid, of 2,2'-dinaphthylmethane-6,6'-disulfonic acid, dibutyl-sulfonic acid or sodium oleylmethyltauride.

Emulsion concentrates are obtained by dissolving the active ingredient in an organic solvent, for example butanol, cyclohexanone, dimethylformamide, xylene, or aromatic hydrocarbons having a higher boiling point. To obtain suspensions or emulsions in water having good properties, wetting agents as specified above are also added.

Dusting powders are obtained by grinding the active ingredient with finely divided, solid substances, for example talc, natural clays such as kaolin, bentonite, pyrophillite, or diatomaceous earths.

Spraying solutions commercially available as aerosol sprays contain the active ingredient dissolved in an organic solvent, and in addition thereto a propellant, for example a mixture of fluorochlorohydrocarbons.

Granules can be produced by atomizing the active ingredient on to an adsorptive, granulated inert material, or by applying concentrates of the active ingredient to the surface of a support, for example sand, kaolinite or a granulated inert material, with the aid of an adhesive, for example polyvinyl alcohol, the sodium salt of polyacrylic acid, or mineral oils. Alternatively, suitable active ingredients may be made into granules, if desired in admixture with fertilizers, in the manner commonly used for the manufacture of granulated fertilizers.

The commercial herbicidal preparations contain varying concentratons of the active ingredients. In wettable powders the concentration of active ingredient varies, for example, from about 10 to 95%, the remainer being the above formulation additives. Emulsion concentrates contain about 10 to 80% of active ingredient, while dusting powders mostly contain 5 to 20% of active ingredient and sprayable solutions about 2 to 20%. In the case of granules, the content of active ingredient partially depends on whether the active ingredient is liquid or solid and on the type of granulation auxiliary or filler used.

Commercial concentrates may be diluted in the usual manner for application. For example, the wettable powder or emulsifiable concentrate may be diluted with water. Dusts and granulated formulations as well as sprayable solutions are not diluted further with an inert substance before their application. The amount applied varies with the external conditions, such as temperature, humidity and the like. In general, about 0.015 to 0.25 gram and preferably about 0.03 to 0.12 gram of active ingredient per square meter are used.

FORMULATION EXAMPLES

EXAMPLE A

A wettable powder which is readily dispersible in water can be obtained by mixing
25 parts by weight of methyl-4-(2'-chloro-4'-bromo-phenoxy)-α-phenoxy-propionate as active ingredient
64 parts by weight of kaolin-containing quartz as inert substance
10 parts by weight of the potassium salt of lignin-sulfonic acid
1 part by weight of sodium oleylmethyl tauride as wetting and dispersing agent,
and grinding the mixture obtained in a disk attrition mill.

EXAMPLE B

A dusting powder having good herbicidal properties can be obtained by mixing
10 parts by weight of methyl-4-(2'-chloro-4'-bromo-phenoxy)-α-phenoxy-propionate as active ingredient
90 parts by weight of talcum as inert substance and grinding the mixture obtained in a cross-beater mill.

EXAMPLE C

An emulsifiable concentrate consists of
15 parts by weight of methyl-4-(2'-chloro-4'-bromo-phenoxy)-α-phenoxy-propionate as active ingredient
75 parts by weight of cyclohexanone as solvent and
10 parts by weight of nonyl (ethoxy)$_{10}$phenol as emulsifier.

The following Examples illustrate the invention.

EXAMPLES OF PREPARATION

EXAMPLE 1

(a)

Methyl-4-(2'-chloro-4'-bromophenoxy)-α-phenoxy-propionate

A 1 liter four necked flask, equipped with reflux condenser, dropping funnel and thermometer, was charged with a solution of 160 g (0.534 mol) of 2-chloro-4-bromo-4'-hydroxydiphenyl ether in 500 ml of dry acetone and, while stirring, 74 g (0.535 mol) of anhydrous $K_2CO_3$ were added in small portions. While stirring was continued, 89.5 g (0.535 mol) of methyl-α-bromo-propionate were added dropwise. When the addition was terminated the temperature was increased until the acetone boiled gently (60°–63° C.) and the mixture was stirred for another 12 hours at that temperature.

After cooling, the precipitated salts were filtered off with suction and washed with acetone. The combined filtrates were evaporated, the remaining oil taken up in 500 ml of petroleum ether (boiling point 60° to 90° C.). The solution was shaken several times with dilute NaOH to remove unreacted starting phenol and finally washed neutral. After drying over $Na_2SO_4$, the petroleum ether was distilled off and the crude ester was fracton-distilled; its boiling point was 195° to 198° C. at 0.4 torr.

168 g (81.4% of the theory) of a yellow-green, limpid oil were obtained ($n_D^{25}=1.5830$) which soon formed colorless crystals (melting point 48° to 49° C.).

The following esters of 4-(2'-chloro-4'-bromophenoxy)-α-phenoxy-propionic acid were prepared in analogous manner using the corresponding α-propionic acid alkyl esters:

(1b) ethyl ester boiling point 185° to 188° C./0.02 torr $n_D^{25}=1.5696$
(1c) isopropyl ester boiling point 185° to 190° C./0.02 torr $n_D^{25}=1.5583$
(1d) n-butyl ester boiling point 186° to 187° C./0.02 torr $n_D^{25}=1.5590$
(1e) isobutyl ester b.p. 210° to 212° C./0.1 torr $n_D^{25}=1.5561$
(1f) sec. butylester
(1g) n-amylester
(1h) n-hexylester
(1i) n-propylester

EXAMPLE 2

4-(2'-Chloro-4'-bromophenoxy)-α-phenoxy-propionic acid 20 g (0.052 mol) of the methyl ester of Example 1 were added dropwise, while stirring, to a solution of 2.2 g of NaOH (0.055 mol) in 100 ml of water. The temperature of the mixture rose slightly and after a few minutes a clear solution was obtained. The temperature was then raised to 80° C. and stirring was continued for 30 minutes. After cooling to room temperature, the mixture was acidified with 2 N HCl (pH 1–2) and the precipitating oily-crystalline acid dissolved in 150 ml of methylene chloride. After separation of the aqueous phase, the $CH_2Cl_2$—solution was washed twice with water, dried over $Na_2SO_4$ and, after distilling off the solvent, the crystalline residue was recrystallized twice from cyclohexane.

16 g (82.8% of the theory) of colorless crystals melting at 117° to 118° C. were obtained.

By reacting the free acids with bases the following salts were obtained:

| | | | |
|---|---|---|---|
| (2b) | $Na^+$ salt | melting point | 135° C. (decomposition) |
| (2c) | $^+NH_3-C_2H_5$ salt | " | 148–49° C. |
| (2d) | $^+NH_2(CH_3)_2$ salt | " | 118–20° C. |
| (2e) | $^+NH_3-CH_2CH_2OH$ salt | " | 119° C. |

BIOLOGICAL EXAMPLES

EXAMPLE I

Seeds of weed grasses were sown in pots filled with loamy soil and placed in the greenhouse for germination and emergence. As soon as the plants had developed 3 or 4 leaves, they were sprayed with wettable powder formulations, suspended in water, of compounds according to the invention.

The results and also the results of all following examples were evaluated 4 weeks later according to the following scheme:

| number | degree of damage in % | | | |
|---|---|---|---|---|
| | weeds | | crop plants | |
| 1 | 100 | | 0 | |
| 2 | 97.5 to | <100 | 0 to | 2.5 |
| 3 | 95.0 to | <97.5 | >2.5 to | 5.0 |
| 4 | 90.0 to | <95.0 | >5.0 to | 10.0 |
| 5 | 85.0 to | <90.0 | >10.0 to | 15.0 |
| 6 | 75.0 to | <85.0 | >15.0 to | 25.0 |
| 7 | 65.0 to | <75.0 | >25.0 to | 35.0 |
| 8 | 32.5 to | <65.0 | >35.0 to | 67.5 |
| 9 | 0 to | <32.5 | >67.5 to | 100 |

4 is still considered an acceptable herbicidal effect in weeds and a satisfactory preserving effect in crop plants (cf. Bolle, Nachrichtenblatt des Deutschen Pflanzenschutzdienstes 16, 1964, pages 92–94).

The results of the experiment are listed in Table I; they show that the tested compounds of the invention, without exception, had a better effect on the weed grasses than comparative compound A. It is especially striking that the effect of the novel compounds on annual blackgrass (Alopecurus) is much better.

An amount of 0.15 to 0.62 kg per hectare of the compound of the invention was sufficient to keep blackgrass satisfactorily under control, whereas an amount of 2.5 kg per hectare of the comparative compound was required to obtain in the same effect.

In a similar experiment crop plants were treated in the same manner with the same formulations. The following crop plants were satisfactorily preserved when treated with an amount of the active compounds of 2.5 kg per hectare: sugar beet, spinach, sunflower, salad, rape, cabbage, peanut, soya, lucerne, pea, horse bean, flax, cotton, tomato, tobacco, celery, carrot and kidney bean.

TABLE I

Effect on weed grasses in a post-emergence trial in pots in the greenhouse (Evaluation scheme)

| compound | kg/ hectare | Alope- curus | Digi- taria | Echino- chloa | Setaria | Lolium |
|---|---|---|---|---|---|---|
| 1a | 2.5 | 1 | 1 | 1 | 1 | 2 |
| | 0.62 | 1 | 1 | 2 | 1 | 3 |
| | 0.15 | 3 | 6 | 2 | 2 | 5 |
| 1d | 2.5 | 1 | 1 | 1 | 1 | 2 |
| | 0.62 | 2 | 1 | 1 | 1 | 4 |
| | 0.15 | 3 | 6 | 2 | 2 | 6 |
| 1b | 2.5 | 1 | 1 | 1 | 1 | 1 |
| | 0.62 | 1 | 1 | 1 | 1 | 2 |
| | 0.15 | 6 | 7 | 1 | 1 | 6 |
| 1c | 2.5 | 1 | 1 | 1 | 1 | 3 |
| | 0.62 | 3 | 4 | 1 | 1 | 4 |
| | 0.15 | 6 | 7 | 1 | 3 | 5 |
| A | 2.5 | 4 | 1 | 2 | 1 | 3 |
| | 0.62 | 7 | 3 | 3 | 2 | 5 |
| | 0.15 | 8 | 8 | 4 | 4 | 7 |

EXAMPLE II

The results of a post-emergence trial in wild oat and wheat which were subjected to natural climatic conditions in an open area (Table II) show that compound 1a had a better effect on wild oat than compound A. Both compounds were used in the form of an emulsion concentrate of 36% strength. The amounts of active compound required for a 90% effect, determined by the probit method (cf. Bliss, Annals of Applied Biology, 22 1935), show very distinctly the difference between the compound of the invention and the comparative compound. When applied in the second stage about half the dosage of the compound of Example 1a, with respect to the comparative compound, was sufficient. None of the compounds did any harm to the wheat.

TABLE II

Effect on wild oatain cereals (evaluation)
Post-emergence treatment in two different stages of development
Experiments in pots on a site without roof

| | | *Avena fatua* | | spring wheat | |
|---|---|---|---|---|---|
| compound | kg/ hectare | stage 1 | stage 2 | stage 1 | stage 2 |
| 1a | 0.9 | 3 | 3 | 2 | 2 |
| | 0.45 | 4 | 4 | 1 | 1 |
| | 0.225 | 5 | 6 | 1 | 1 |
| | 0.112 | 6 | 7 | 1 | 1 |
| A | 0.9 | 3 | 5 | 1 | 1 |
| | 0.45 | 5 | 5 | 1 | 1 |
| | 0.225 | 8 | 7 | 1 | 1 |
| | 0.112 | 9 | 8 | 1 | 1 |

90% effective dose in kg per hectare found with the aid of a graph
active compound of Ex. 1a     0.34 in stage 1     0.45 in stage 2

TABLE II-continued

Effect on wild oatain cereals (evaluation)
Post-emergence treatment in two different stages of development
Experiments in pots on a site without roof

| | | Avena fatua | | spring wheat | |
|---|---|---|---|---|---|
| compound | kg/ hectare | stage 1 | stage 2 | stage 1 | stage 2 |
| comparative compound A | | 0.55 in stage 1 | | 0.82 in stage 2 | | stage 1: 3 to 4 leaves with beginning growth of side shoots
stage 2: main tillering to terminated tillering.

TABLE III

Effect on wild oat and sugar beet
Post emergence treatment in two stages of development
boxes 20 × 24 × 22 cm in size on a site without roof

| | | Avena fatua | | |
|---|---|---|---|---|
| Compound | kg/ hectare | number | degree of damage % (evaluation by weight) | sugar beet number |
| | | 3-leaf stage | | 2-leaf stage |
| 1a | 0.9 | 1 | 100 | 2 |
| A | 0.9 | 2 | 99 | 2 |
| | | start of tillering | | 4-leaf stage |
| 1a | 0.9 | 3 to 4 | 96 | 2 |
| A | 0.9 | 5 | 79 | 2 |

EXAMPLE IV

In summer a further experiment was carried through under similar conditions to compare the effect of compound 1a with that of comparative compound A. Both compounds were used in the form of an emulsion concentrate (Table IV). In two types of wild oat, i.e. Avena fatua and Avena ludoviciana, the compound of Example 1a had a distinctly better effect than the comparative compound. The difference was still higher in annual black-grass (Alopecurus) which responded very well to compound 1a but little to the comparative compound A. Barley and wheat remained undamaged.

TABLE IV

Effect on types of wild oat and blackgrass in cereals
Post-emergence treatment (evaluation scheme); experiment in pots on a site without roof

| compound | kg/ hectare | Avena fatua | Avena ludo- vici- ana | Alopecu- rus myos. | spring wheat | spring barley |
|---|---|---|---|---|---|---|
| | 0.9 | 5 | 4 | 1 | 1 | 1 |
| 1a | 0.45 | 6 | 5 | 3 | 1 | 1 |
| | 0.225 | 7 | 6 | 5 | 1 | 1 |
| | 0.9 | 6 | 6 | 4 | 1 | 1 |
| A | 0.45 | 8 | 7 | 6 | 1 | 1 |
| | 0.225 | 8 | 7 | 8 | 1 | 1 |

EXAMPLE V

In a greenhouse the compounds to be tested were sprayed on the surface of the soil directly after sowing. The result of the pre-emergence treatment with compound 1a and comparative compound A is listed in Table V indicating that compound 1a had a better effect. Dicotyledonous crop plants (the same as used in Example I) were not damaged by the applied amounts.

Analogous results were obtained with the compounds of Examples 1b, 1c and 1d.

TABLE V

Effect on weed grasses in a pre-emergence process (evaluation scheme) experiment in pots in the greenhouse.

| Compound | kg/ hectare | Digitaria | Echinochloa | Lolium | Setaria |
|---|---|---|---|---|---|
| 1a | 1.25 | 2 | 2 | 3 | 4 |
| | 0.62 | 4 | 3 | 6 | 6 |
| A | 1.25 | 4 | 3 | 5 | 6 |
| | 0.62 | 7 | 4 | 6 | 8 |

EXAMPLE VI

In a field trial compound 1a of the invention was sprayed in the form of a 36% wettable powder formulation onto wild oat (single system, natural growth) after the plants had developed 3 or 4 leaves.

Three lots each were treated with different concentrations of the active compound and the comparative compound, the amount of spray liquor applied being 600 liters per hectare. The average values are indicated in Table VI. Besides the usual visual evaluation at the end of the trial, the number of panicles per square meter was counted. In the untreated lots 400 to 500 panicles were counted per square meter, i.e. the field was heavily infected.

The results show that the effect of the comparative compound was insufficient in a concentration of 0.90 kg per hectare while the compound of the invention combated the wild oat satisfactorily or very satisfactory in a concentration of from 0.72 to 0.90 kg per hectare.

TABLE VI

Field trial in wild oat, post-emergence treatment

| Compound | kg/ hectare | evaluation 5 weeks after treatment | efficiency in % (counting of panicles) |
|---|---|---|---|
| 1a | 0.54 | 7 | 79.0 |
| | 0.72 | 5 | 90.0 |
| | 0.90 | 3 | 97.4 |
| A | 0.54 | 8 | 50.7 |
| | 0.72 | 7 | 59.9 |
| | 0.90 | 6 | 65.2 |

The relations are still more distinct when the amount of active compound required for a 90% effect is determined by the probit method (graphical evaluation) mentioned in Example II.

| compound 1a | without wetting agent | 0.68 kg/hectare |
|---|---|---|
| compound A | without wetting agent | 2.7 kg/hectare |

Hence, compared with the comparative compound, about ¼ of compound 1a was sufficient.

EXAMPLE VII

In a greenhouse some of the compounds of the invention were sprayed on plants of wild oat, the compounds being used as emulsion concentrates. 4 Weeks after the treatment the results summarized in Table VII were evaluated. It can be seen that all compounds had a very good effect on wild oat in a relatively low concentration.

EXAMPLE VIII

In a similar trial some of the compounds of the invention were sprayed in the form of wettable powder formulations on barnyard grass in the 3 to 4 leaf-stage.

Table VIII shows that all compounds had a good to very good effect.

TABLE VII

Post-emergence trial in the greenhouse
Effect on wild oat 4 weeks after treatment
Dose 31 kg/hectare of active compound (as emulsion concentrate)

| Compound of Example | effect (number) |
|---|---|
| (1a) | 1 |
| (1b) | 1 |
| (1c) | 1 |
| (1d) | 1 |
| (1e) | 2 |

TABLE VIII

Post-emergence trial in the greenhouse
Effect on barnyard grass 4 weeks after treatment
Dose 31 kg/hectare of active compound (as wettable powder formulation)

| Compound of Example | effect (number) |
|---|---|
| (1c) | 1 |
| (2b) | 3 |
| (2c) | 1 |
| (2d) | 1 |
| (2e) | 4 |

What is claimed is:

1. Compounds of the formula I

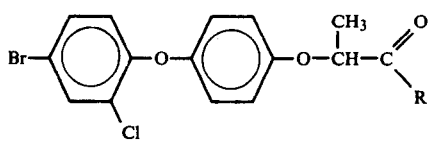

in which R represents hydroxyl, $(C_1-C_{10})$ alkoxy, but not the iso-propoxy or n-butoxy member thereof, $(C_1-C_6)$-alkylthio, $(C_2-C_4)$ alkenyloxy, cyclohexyloxy, cyclopentyloxy, phenoxy or phenylthio both optionally substituted once or twice with halogen, benzyloxy, benzylthio or -O-cat in which "cat" stands for the cation of an inorganic or organic base.

2. A compound as claimed in claim 1, wherein R is [$(C_1-C_6)$-alkoxy] methoxy, ethoxy, or isobutoxy, or O-cat.

3. A compound as claimed in claim 1, which is methyl 2-[4-(2'-chloro-4'-bromophenoxy)]-phenoxypropionate.

4. A compound as claimed in claim 1, which is ethyl 2-[4-(2'-chloro-4'-bromophenoxy)]-phenoxypropionate.

5. A compound as claimed in claim 1, which is isobutyl 2-[4-(2'-chloro-4'-bromophenoxy)]-phenoxypropionate.

6. A herbidical composition containing a carrier and as active ingredient an effective amount of a compound of claim 1.

7. A compound of the formula

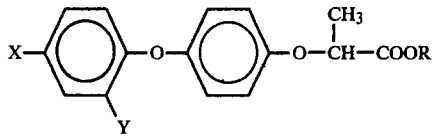

wherein X is —Br and Y is —Cl and R is methyl, ethyl or isobutyl.

8. A method for combating weed grasses, comprising applying an effective amount of a compound as defined in claim 7 to a locus having undesirable weed grasses sought to be combated.

9. A herbicidal composition containing a carrier and, as an active ingredient, an effective amount of a compound as defined in claim 7.

10. The method as defined in claim 8, wherein the weed sought to be combated is annual blackgrass.

11. The method as defined in claim 8, wherein the weed sought to be combated is crabgrass.

12. A method for combating weed grasses, comprising applying an effective amount of the compound as defined in claim 3 to a locus having an undesirable weed sought to be combated.

13. A method for combating weed grasses, comprising applying an effective amount of the compound as defined in claim 4 to a locus having an undesirable weed sought to be combated.

14. A method for combating weed grasses, comprising applying an effective amount of the compound as defined in claim 7 to a locus having an undesirable weed sought to be combated.

* * * * *